US00PP36442P2

(12) United States Plant Patent
Bernuetz

(10) Patent No.: US PP36,442 P2
(45) Date of Patent: Feb. 11, 2025

(54) ***EUPHORBIA* PLANT NAMED 'BONPRI 1762'**

(50) Latin Name: ***Euphorbia pulcherrima Willd.* ex *Klotzsch* X *Euphorbia cornastra***
Varietal Denomination: BONPRI 1762

(71) Applicant: Andrew Bernuetz, Glenbrook (AU)

(72) Inventor: Andrew Bernuetz, Glenbrook (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/621,014

(22) Filed: Mar. 28, 2024

(51) Int. Cl.
*A01H 5/12* (2018.01)
*A01H 6/38* (2018.01)

(52) U.S. Cl.
USPC ..... Plt./307

(58) Field of Classification Search
USPC ..... Plt./303, 307
See application file for complete search history.

*Primary Examiner* — Susan McCormick Ewoldt
(74) *Attorney, Agent, or Firm* — C. Anne Whealy

(57) ABSTRACT

A new and distinct cultivar of Euphorbia plant named 'BONPRI 1762', characterized by its relatively compact, upright and mounded plant habit; vigorous growth habit; freely branching habit; inflorescences with bright red-colored flower bracts; and good post-production longevity.

2 Drawing Sheets

Figure 1:
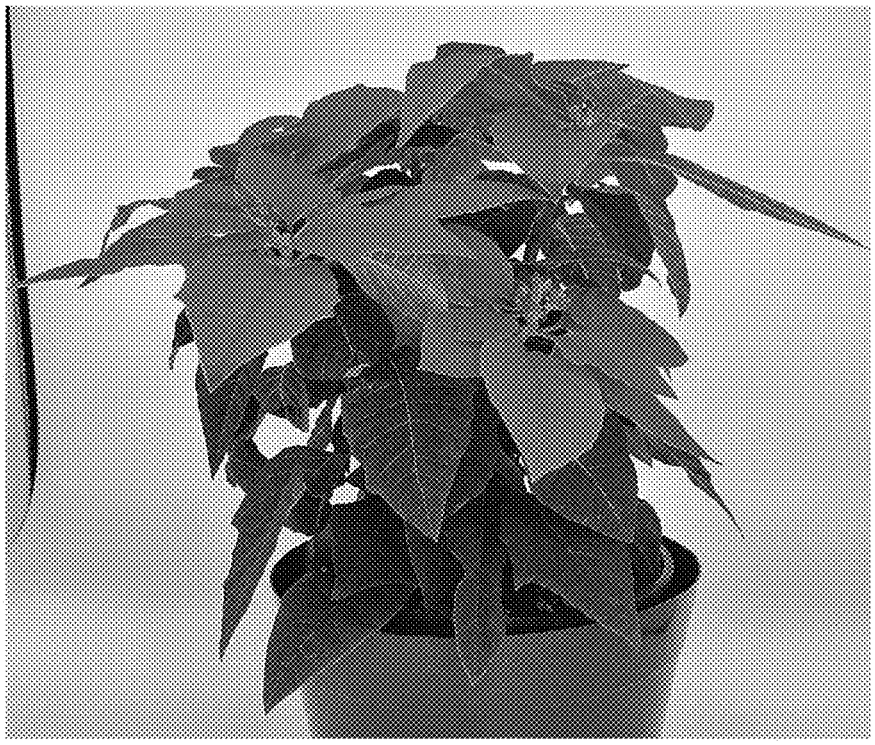

Botanical designation: *Euphorbia pulcherrima Willd.* ex *Klotzsch* X *Euphorbia cornastra.*
Cultivar denomination: 'BONPRI 1762'.

STATEMENT REGARDING PRIOR DISCLOSURES BY THE INVENTOR/APPLICANT & ASSIGNEE

The Inventor/Applicant and Assignee, Bonza Botanicals Pty., Ltd. of Yellow Rock, New South Wales, Australia, hereby confirm that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102 (b) (1) for disclosure and/or sales prior to the filing date but less than one year prior to the effective filing date.

BACKGROUND OF THE INVENTION

The present invention relates to a new and distinct cultivar of Euphorbia plant, an interspecific hybrid botanically known as *Euphorbia pulcherrima Willd.* ex *Klotzsch* X *Euphorbia cornastra*, and hereinafter referred to by the cultivar name 'BONPRI 1762'.

The new Euphorbia plant is a product of a planned breeding program conducted by the Inventor in Yellow Rock, New South Wales, Australia. The objective of the program is to create and develop new interspecific Euphorbia plants with compact, upright and mounded plant habit and attractive flower bracts.

The new Euphorbia plant is a naturally-occurring whole plant mutation of a proprietary selection of *Euphorbia pulcherrima Willd.* ex *Klotzsch* X *Euphorbia cornastra* identified as code number 15-16, not patented. The new Euphorbia plant was discovered and selected by the Inventor as a single flowering plant from within a population of plants of the mutation parent selection in a controlled greenhouse environment in Yellow Rock, New South Wales, Australia in April, 2017.

Asexual reproduction of the new Euphorbia plant by terminal vegetative cuttings in a controlled greenhouse environment in Yellow Rock, New South Wales, Australia since September, 2017 has shown that the unique features of this new Euphorbia plant are stable and reproduced true to type in successive generations of asexual reproduction.

SUMMARY OF THE INVENTION

Plants of the new Euphorbia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BONPRI 1762'. These characteristics in combination distinguish 'BONPRI 1762' as a new and distinct Euphorbia plant:

1. Relatively compact, upright and mounded plant habit.
2. Vigorous growth habit.
3. Freely branching habit.
4. Inflorescences with bright red-colored flower bracts.
5. Good post-production longevity.

Plants of the new Euphorbia differ primarily from plants of the mutation parent selection in flower bract color as flower bracts of plants of the new Euphorbia are bright red in color whereas flower bracts of plants of the mutation parent selection are red in color with numerous and random white-colored spots. In addition, plants of the new Euphorbia are not as freely branching as plants of the mutation parent selection.

Plants of the new Euphorbia can be compared to plants of the *Euphorbia pulcherrima Willd.* ex *Klotzsch* X *Euphorbia cornastra* 'Bonpridepcom', disclosed in U.S. Plant Pat. No.

21,324. In side-by-side comparisons, plants of the new Euphorbia differ primarily from plants of 'Bonpridepcom' in the following characteristics:

1. Plants of the new Euphorbia are larger and more vigorous than plants of 'Bonpridepcom'.
2. Plants of the new Euphorbia have shorter leaves than plants of 'Bonpridepcom'.
3. Plants of the new Euphorbia have flatter inflorescences than plants of 'Bonpridepcom'.
4. Plants of the new Euphorbia have smaller flower bracts than plants of 'Bonpridepcom'.
5. Plants of the new Euphorbia and 'Bonpridepcom' differ in flower bract color as flower bracts of plants of the new Euphorbia are bright red in color whereas flower bracts of plants of 'Bonpridepcom' are dark red purple in color.

BRIEF DESCRIPTION OF THE PHOTOGRAPHS

The accompanying photographs illustrate the overall appearance of the new Euphorbia plant showing the colors as true as it is reasonably possible to obtain in colored reproductions of this type. Colors in the photographs may differ slightly from the color values cited in the detailed botanical description which accurately describe the colors of the new Euphorbia plant.

The photograph on the first sheet (FIG. 1) is a side perspective view of a typical flowering plant of 'BONPRI 1762' grown in a container.

Figure 2:
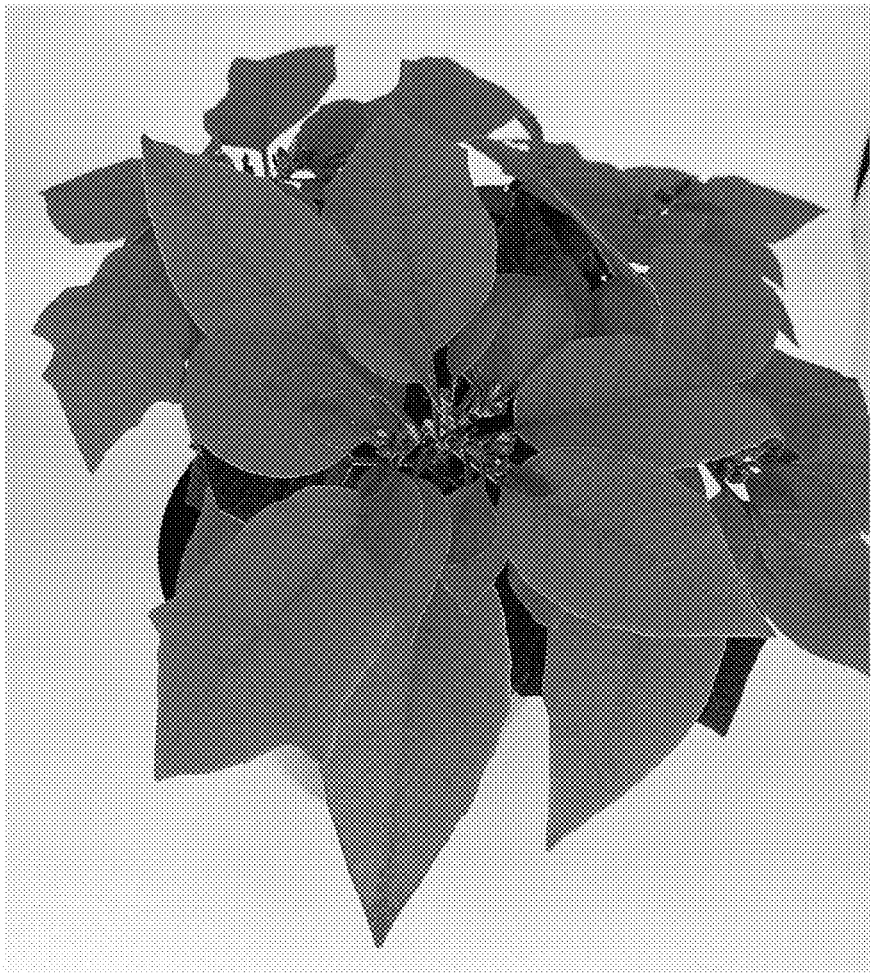

The photograph on the second sheet (FIG. 2) is a close-up view of a typical flowering plant of 'BONPRI 1762'.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial Euphorbia production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima Willd.* ex *Klotzsch* X *Euphorbia cornastra* 'BONPRI 1762'.

Parentage: Naturally-occurring whole plant mutation of a proprietary selection of *Euphorbia pulcherrima Willd.* ex *Klotzsch* X *Euphorbia cornastra* identified as code number 15-16, not patented.

Propagation:

*Type*.—Terminal vegetative cuttings.

*Time to initiate roots, summer*.—About ten days at temperatures about 20° C. to 21° C.

*Time to initiate roots, winter*.—About twelve days at temperatures about 20° C. to 21° C.

*Time to produce a rooted young plant, summer*.—About 24 days at temperatures about 20° C. to 21° C.

*Time to produce a rooted young plant, winter*.—About 28 days at temperatures about 20° C. to 21° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Relatively compact, upright and mounded plant habit; inverted triangle; inflorescences positioned above the foliar plane; vigorous growth habit.

*Plant height*.—About 19 cm.

*Plant diameter or spread*.—About 26 cm.

*Lateral branch description*.—Branching habit: Freely branching habit, about five to six lateral branches develop per plant. Length: About 10.8 cm. Diameter: About 3.5 mm. Internode length: About 1.2 cm. Aspect: Mostly upright to slightly outwardly. Strength: Moderately strong. Texture: Smooth, glabrous. Color: Close to 144A.

*Leaf description*.—Arrangement: Alternate, simple. Length: About 6.8 cm. Width: About 4.7 cm. Shape: Lanceolate. Apex: Acute. Base: Rounded. Margin: Mostly entire, occasionally with few shallow lobes; undulate. Venation pattern: Pinnate, reticulate. Texture, upper surface: Smooth, glabrous. Texture, lower surface: Rough, glabrous. Color: Developing leaves, upper surface: Close to 139A. Developing leaves, lower surface: Close to 137B. Fully developed leaves, upper surface: Close to 139A; venation, close to 143A. Developing and fully developed leaves, lower surface: Close to NN137B; venation, close to 143C.

*Petioles*.—Length: About 1.6 cm. Diameter: About 1.6 mm. Texture, upper and lower surfaces: Smooth, glabrous. Color, upper and lower surfaces: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about five to six inflorescences develop per plant.

*Inflorescence diameter*.—About 15.8 cm.

*Inflorescence height*.—About 4.8 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 49 to 50 days under natural season or photoinductive conditions in Japan.

*Post-production longevity*.—Good post-production longevity; plants of the new Euphorbia maintain good substance and bract color for about six to eight weeks.

*Flower bracts*.—Quantity per inflorescence: About 16. Length, largest bracts: About 6.5 cm. Width, largest bracts: About 2.6 cm. Aspect: Mostly horizontal and flat. Shape: Elliptic. Apex: Acute. Base: Obtuse. Margin: Entire. Texture and luster, upper and lower surfaces: Smooth, glabrous; matte. Venation pattern: Pinnate, reticulate. Color: Transitional bracts, upper surface: Random sectors, close to 202A and 45C. Transitional bracts, lower surface: Random sectors, close to 147B and 64C. Developing bracts, upper surface: Close to 46B. Developing bracts, lower surface: Close to 45C. Fully expanded bracts, upper surface: Close to 45B; venation, close to 45A; flower bracts resist fading with subsequent development. Fully expanded bracts, lower surface: Close to 47B; venation, close to 50C; flower bracts resist fading with subsequent development. Flower bract petioles: Length: About 6 mm. Diameter: About 1.2 mm. Texture, upper and lower surfaces: Smooth, glabrous. Color, upper and lower surfaces: Close to N45C.

*Cyathia*.—Quantity per corymb: About 14. Diameter of cyathia cluster: About 2.7 cm. Height, individual cyathium: About 4.8 mm. Diameter, individual cyathium: About 5.3 mm. Shape, individual cyathium: Globose. Color: Distally, close to 187A, and proximally, close to 142B. Nectaries: Quantity per cyathium: About eight. Size: About 2.1 mm by 3.3 mm. Texture: Smooth, glabrous. Color: Close to 45C.

*Peduncles*.—Length: About 2.2 mm. Diameter: About 1.8 mm. Texture, upper and lower surfaces: Smooth, glabrous. Aspect: Mostly upright. Color, upper and lower surfaces: Close to 142B.

*Reproductive organs*.—To date, stamen and pistil development have not been observed on plants of the new Euphorbia.

*Seeds and fruits*.—To date, seed and fruit development have not been observed on plants of the new Euphorbia.

Pathogen & pest resistance: To date, plants of the new Euphorbia have not been shown to be resistant to pathogens and pests common to Euphorbia plants.

Temperature tolerance: Plants of the new Euphorbia have been observed to tolerate temperatures ranging from about 8° C. to about 40° C.

It is claimed:

1. A new and distinct Euphorbia plant named 'BONPRI 1762' as herein illustrated and described.

* * * * *